United States Patent [19]

Ager et al.

[11] 4,279,912
[45] Jul. 21, 1981

[54] NOVEL IMIDAZOQUINOLINES

[75] Inventors: Ian R. Ager; Peter J. Ramm, both of Swindon, England

[73] Assignee: Roussel Uclaf, Paris, France

[21] Appl. No.: 869,842

[22] Filed: Jan. 16, 1978

[30] Foreign Application Priority Data

Jan. 20, 1977 [GB] United Kingdom ............ 2377/77

[51] Int. Cl.³ .................. A61K 31/47; C07D 471/14
[52] U.S. Cl. .......................... 424/258; 424/248.55; 424/250; 546/84; 544/126; 544/361
[58] Field of Search ............ 424/258, 250, 248.55; 260/287 CF; 546/84; 544/126, 361

[56] References Cited

U.S. PATENT DOCUMENTS

| | | | |
|---|---|---|---|
| 3,624,093 | 11/1971 | Sulkowski et al. | 260/288 CF |
| 4,075,343 | 2/1978 | Kadin | 260/287 CF |

*Primary Examiner*—Donald G. Daus
*Assistant Examiner*—Diana G. Rivers
*Attorney, Agent, or Firm*—Hammond & Littell, Weissenberger and Muserlian

[57] ABSTRACT

Novel imidazoquinolines of the formula

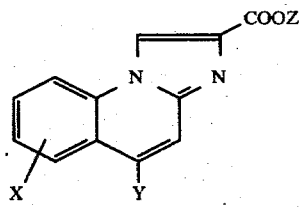

wherein X and Y are individually selected from the group consisting of hydrogen, halogen and alkoxy of 1 to 5 carbon atoms, Z is selected from the group consisting of hydrogen, alkyl of 1 to 5 carbon atoms optionally substituted with at least two hydroxyls or protected hydroxyls and

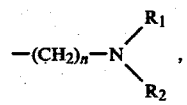

n is an integer from 1 to 6 and $R_1$ and $R_2$ are individually alkyl of 1 to 5 carbon atoms and taken together with the nitrogen to which they are attached form a saturated heterocyclic ring containing 4 to 6 carbon atoms and optionally interrupted by another heteroatom which further heteroatom is optionally substituted with alkyl of 1 to 5 carbon atoms and non-toxic, pharmaceutically acceptable salts thereof having antiallergic and bronchodilatory activity and their preparations.

24 Claims, No Drawings

NOVEL IMIDAZOQUINOLINES

STATE OF THE ART

Copending, commonly assigned U.S. patent application Ser. No. 799,580 filed May 23, 1977, now abandoned, describes imidazobenzoxazines having antiallergic and bronchodilatory activity.

OJECTS OF THE INVENTION

It is an object of the invention to provide the novel compounds of formula I and their non-toxic, pharmaceutically acceptable salts thereof and to provide a novel process for the preparation of the said compounds.

It is another object of the invention to provide novel antiallergic and bronchodilatory compositions and to provide a novel method of inducing antiallergic and bronchodilatory activity in warm-blooded animals.

These and other objects and advantages of the invention will become obvious from the following detailed description.

THE INVENTION

The novel imidazoquinolines of the invention are selected from the group consisting of compounds of the formula

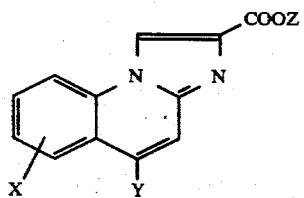

I wherein X and Y are individually selected from the group consisting of hydrogen, halogen and alkoxy of 1 to 5 carbon atoms, Z is selected from the group consisting of hydrogen, alkyl of 1 to 5 carbon atoms optionally substituted with at least two hydroxyls or protected hydroxyls and

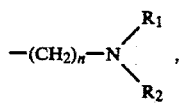

n is an integer from 1 to 6 and $R_1$ and $R_2$ are individually alkyl of 1 to 5 carbon atoms and taken together with the nitrogen to which they are attached form a saturated heterocyclic ring containing 4 to 6 carbon atoms and optionally interrupted by another heteroatom which further heteroatom is optionally substituted with alkyl of 1 to 5 carbon atoms and non-toxic, pharmaceutically acceptable salts thereof.

When X is halogen, it may be bromine but is preferably chlorine and when X is alkoxy of 1 to 5 carbon atoms, the preferred group is methoxy. When Y is halogen, it is preferably bromine or chlorine and when Y is alkoxy of 1 to 5 carbon atoms, it is preferably methoxy or isopropoxy.

Suitable groups of Z are alkyl of 1 to 5 carbon atoms such as methyl, ethyl, propyl, isopropyl, butyl, tert.-butyl and pentyl optionally substituted with two or more hydroxyl groups or protected hydroxy groups such as ether groups like tetrahydropyranyloxy. When the hydroxyl groups are vicinal, the hydroxyl groups may form part of a dioxolane as in a ketonide of 3 to 6 carbon atoms like an acetonide. Therefore, an example of Z is 2,3-dihydroxy-propyl or the acetonide derivative thereof, (2,2-dimethyl-1,3-dioxolan-4-yl)methyl.

Examples of the heterocyclic groups formed by $R_1$ and $R_2$ together with the nitrogen atom to which they are attached are saturated heterocyclic rings of 4 to 6 ring carbon atoms optionally interrupted with another heteroatom optionally substituted with an alkyl of 1 to 5 carbon atoms. Specific heterocyclic groups of this type are pyrrolidino, piperidino, morpholino, piperazinyl, N-methyl-piperazinyl, N-ethyl-piperazinyl, N-propyl-piperazinyl and N-butyl-piperazinyl.

As the compounds of formula I are basic in nature, they may also be present in the form of non-toxic, pharmaceutically acceptable acid addition salts of inorganic acids such as hydrochloric acid, hydrobromic acid, hydroiodic acid, nitric acid, sulfuric acid or phosphoric acid or organic acids such as acetic acid, formic acid, benzoic acid, maleic acid, fumaric acid, succinic acid, tartaric acid, citric acid, oxalic acid, glyoxalic acid or aspartic acid or alkane sulfonic acids such as methanesulfonic acid or arylsulfonic acids such as benzenesulfonic acid.

The compounds of formula I wherein Z is hydrogen will form salts with bases or metal ions. Examples of said salts are alkali metals such as sodium potassium and lithium, alkaline earth metals such as calcium, metals such as aluminium or magnesium, ammonium, amines such as lysine, arginine, triethanolamine or tris(hydroxymethyl)aminomethane.

Among the preferred compounds of the invention are those of formula I wherein X is hydrogen, chlorine or methoxy and Z is hydrogen or alkyl of 1 to 5 carbon atoms, especially 1 to 3 carbon atoms, those wherein Y is hydrogen, chlorine, methoxy or isopropoxy and especially those wherein Z is hydrogen or ethyl and Y is hydrogen, chlorine or isopropoxy.

Particularly preferred compounds of the invention are imidazo-[1,2-a]-quinoline-2-carboxylic acid, 5-chloroimidazo-[1,2-a]-quinoline-2-carboxylic acid, 8-chloroimidazo-[1,2-a]-quinoline-2-carboxylic acid, 5-chloro-8-methoxyimidazo-[1,2-a]-quinoline-2-carboxylic acid, 8-chloro-5-isopropoxyimidazo-[1,2-a]-quinoline-2-carboxylic acid, 8-methoxyimidazo-[1,2-a]-quinoline-2-carboxylic acid, 5,8-dichloroimidazo-[1,2-a]-quinoline-2-carboxylic acid and 8-bromo-5-chloroimidazo[1,2-a]-quinoline-2-carboxylic acid and non-toxic, pharmaceutically acceptable salts thereof.

The novel process of the invention for the preparation of the compounds of formula I wherein Z is alkyl of 1 to 5 carbon atoms optionally substituted with 2 or more protected hydroxyl groups comprises cyclizing a compound of the formula

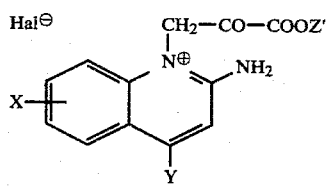

II wherein X and Y have the above definition, Z' is an alkyl of 1 to 5 carbon atoms optionally substituted by two or more protected hydroxy radicals and Hal is a halogen such as chlorine or bromine to form the desired compound of formula I. The cyclization may be effected by heating the compound of formula II, preferably in the presence of an organic solvent such as ethanol and preferably at the boiling temperature of the reaction mixture.

The compound of formula II may be obtained by reaction of a compound of the formula

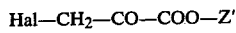   III wherein Hal and Z' have the above definitions with a compound of the formula

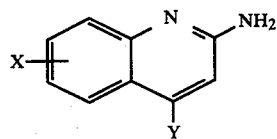   IV wherein X and Y have the above definition, conveniently in the presence of an organic solvent such as an ether solvent e.g. dimethoxymethane, dimethoxyethane, dioxane or tetrahydrofuran.

The compounds of formula I wherein X and Y, which may be the same or different, are hydrogen or an alkoxy of 1 to 5 carbon atoms and Z is alkyl of 1 to 5 carbon atoms optionally substituted by two or more protected hydroxy radicals may be prepared by heating a compound of the formula

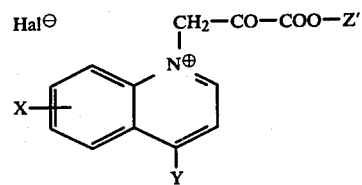   V wherein X, Y, Z' and Hal have the above definitions with an ammonium or a hydroxylamine salt, e.g. a salt of an organic acid such as acetic acid or a salt of an inorganic acid such as hydrochloric acid, sulfuric acid or phosphoric acid. The reaction is preferably effected in the presence of acetic acid as the solvent and most preferably at the boiling temperature of the reaction mixture.

The compounds of formula V may be prepared by reaction of a compound of formula III as hereinbefore defined with a compound of the formula

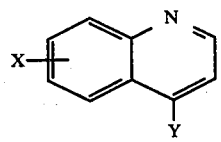   VI wherein X and Y have the above definitions. The reaction is conveniently effected in the presence of an organic solvent such as a mixture of dimethoxyethane and ether and conveniently at ambient temperatures.

The compounds of formula I wherein Z is hydrogen may be prepared by hydrolysis of a compound of formula I as above defined wherein Z is alkyl optionally substituted by two or more protected hydroxy radicals. The hydrolysis may be effected with an alkali metal hydroxide such as sodium hydroxide or potassium hydroxide. The compounds of formula I wherein Z is

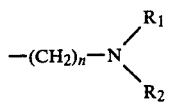

in which n, $R_1$ and $R_2$ have the above definitions or alkyl of 1 to 5 carbon atoms optionally substituted by two or more protected hydroxy radical may be prepared by reaction of an acid of formula I defined above wherein Z is hydrogen atom or an esterifying derivative thereof a compound of the formula

HO—Z''   VII wherein Z'' is

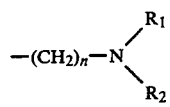

in which n, $R_1$ and $R_2$ have the above definitions or alkyl of 1 to 5 carbon atoms optionally substituted by two or more protected hydroxy radicals or an esterifying derivative thereof whereby the desired ester of formula I is obtained. Thus, for example, an acid halide such as chloride of the acid of formula I may be reacted with the alcohol of formula VII in the presence of an acid binding agent, e.g. a base such as triethylamine. The acid halide may be produced from the acid of formula I by reaction with a suitable halogenating agent such as thionyl chloride. The esterification is preferably effected in the presence of an anhydrous organic solvent such as dichloromethane or diethyl ether.

As will be appreciated, the radical Z'' in the compound of formula VII may carry protected hydroxy radicals. Such protecting groups may, if desired, be removed after completion of the reaction. By the use of appropriate protecting groups, these may be removed selectively.

The compounds of formula I wherein Z is alkyl of 1 to 5 carbon atoms substituted by two or more hydroxy radicals may be prepared by deprotection of an appropriate compound of formula I as hereinbefore defined wherein Z is alkyl of 1 to 5 carbon atoms substituted by two or more protected hydroxy radicals. The hydroxy protecting groups may, for example, be removed by hydrolysis with an organic or mineral acid as in the case of dioxolane groups or tetrahydropyranyloxy groups.

The compounds of formula I wherein Z is alkyl of 1 to 5 carbon atoms substituted by two or more protected hydroxy radicals may be prepared by reaction of a compound of formula I as hereinbefore defined wherein Z is alkyl of 1 to 5 carbon atoms substituted by two or more hydroxy radicals with an appropriate hydroxy protecting agent. Suitable hydroxy-protecting agents include, for example, etherifying agents, such as dihydropyran. When it is desired to protect two vicinal hydroxy radicals, the compound of formula I may be reacted, for example, with a ketone or aldehyde thus forming a cyclic ketal or acetal, i.e. dioxolane, group.

The compounds of formula I may, if desired, be converted into the acid addition salts thereof by reaction with an appropriate acid such as those exemplified hereinbefore, preferably in substantially equimolar quantities. Compounds of formula I wherein Z is hydrogen may, if desired, be converted into the base addition salts thereof by reaction with an appropriate organic or inorganic base.

The preparation of 2-amino-4-alkoxyquinolines from 2-amino-4-hydroxyquinoline is described by Grout et al [J. Chem. Soc. Perkin I, (1973), p. 1314]. The preparation of 2-amino-4-chloroquinolines from 2-amino-4-hydroxyquinolines is described by Hardman et al [J. Chem. Soc. (1958), p. 614]. The remaining compounds of formula IV may be prepared by analogous methods.

The novel antiallergic and bronchodilatory compositions of the invention are comprised of an antiallergically and bronchodilatory effective amount of at least one compound of formula I and their non-toxic, pharmaceutically acceptable salts and an inert pharmaceutical carrier or excipient. The compositions may be in the form of tablets, coated tablets, gelatin capsules, granules, suppositories, syrups, aerosols, creams, ointments and injectable solution or suspensions.

Examples of suitable excipients are talc, gum arabic, lactose, starch, magnesium stearate, cacao butter, aqueous and non-aqueous vehicles, fatty substances of animal or vegetable origin, paraffinic derivatives, glycols, preservatives and diverse wetting agents, dispersants and emulsifiers.

The compositions due to their antiallergic and bronchodilatory activity are useful for the treatment of asthma and bronchial asthma of an allergic origin.

The novel method of the invention for inducing antiallergic and bronchodilatory activity in warm-blooded animals including humans comprises administering to warm-blooded animals an antiallergically and bronchodilatory effective amount of at least one compound of formula I and their non-toxic, pharmaceutically acceptable salts. The said compounds may be administered orally, rectally, topically or parenterally and the usual daily dose is 0.005 to 1 mg/kg depending on the specific compound and the method of treatment.

In the following examples there are described several preferred embodiments to illustrate the invention. However, it should be understood that the invention is not intended to be limited to the specific embodiments.

EXAMPLE 1 ethyl imidazo-[1,2-a]-quinoline-2-carboxylate 8.0 g of ethyl bromopyruvate were added to a solution of 5.0 g of quinoline in 50 ml of a 1-1 dimethoxyethane-ether mixture and the mixture was allowed to stand at room temperature overnight. The quaternary salt thus precipitated was filtered off, was washed with ether and then was dissolved in 40 ml of glacial acetic acid. 8 g of ammonium acetate were added to the solution and the mixture was heated at reflux for 4 hours. The mixture was subsequently poured into 300 ml of water and the mixture thus formed was adjusted to a pH of 9-10 with solid sodium carbonate. The mixture was extracted with chloroform and the chloroform extract was dried over magnesium sulfate and evaporated to dryness under reduced pressure. The oil residue was chromatographed over silica gel and was eluted with ethyl acetate to obtain two products. The less polar material was identified as ethyl imidazo-[1,2-a]-quinoline-2-carboxylate (1) and the more polar material as ethyl 4,5-dihydroimidazo-[1,2-a]-quinoline-2-carboxylate (2) and both products were crystallized from ether.

(1) Analysis $C_{14}H_{12}N_2O_2$. Calculated: %C 69.99; %H 5.03; %N 11.66; Found: C 70.06; H 4.99; N 11.66
melting point of 174°-6° C.
I.R. (KBr Disc): 3145 cm$^{-1}$ (C—H$_1$ stretch) 1702 cm$^{-1}$ (Ester C=O)

Analysis: $C_{14}H_{14}N_2O_2$. Calculated: %C 69.41; %H 5.82; %N 11.56; Found: C 69.24; H 5.85; N 11.41
melting point of 126°-8° C.
I.R. (KBr Disc): 3145 cm$^{-1}$ (C—H$_1$ stretch); 1706 cm$^{-1}$ (Ester C=O)

EXAMPLE 2 imidazo-[1,2-a]-quinoline-2-carboxylic acid hydrochloride 0.5 g of ethyl imidazo-[1,2-a]-quinoline-2-carboxylate was dissolved in 50 ml of ethanol and then a solution of 0.12 g of sodium hydroxide in 10 ml of water was added thereto. The mixture was heated on a steam bath for 2 hours and was subsequently acidified to a pH of 2 with concentrated hydrochloric acid. The mixture was evaporated to dryness under reduced pressure and 50 ml of methanol were added to the residue. The solution was filtered to remove inorganic material and the filtrate was evaporated to dryness under reduced pressure. The residue was crystallized by trituration in chloroform to give imidazo-[1,2-a]-quinoline-2-carboxylic acid in the form of the hydrochloride salt.

Analysis: $C_{12}H_9Cl\ N_2O_2$. melting at 254°-8° C.
I.R. (KBr Disc): 3200-2100 cm$^{-1}$ (Acid, N$^+$H); 3145 cm$^{-1}$ (C—H$_1$ stretch); 1722 cm$^{-1}$ (acid C=O)

EXAMPLE 3 ethyl 5-methoxyimidazo-[1,2-a]-quinoline-2-carboxylate 350 mg of 2-amino-4-methoxyquinoline [Grout et al., J. C. S. Perkin I, (1973), p. 1314] were dissolved in 10 ml dimethoxyethane and 390 mg of ethyl bromopyruvate were added thereto. The crystalline intermediate thus formed was filtered off, washed with ether and then was dissolved in ethanol. The solution obtained was refluxed for 1 hour and then the solvent was removed under vacuum. The residue was purified by column chromatography (silica gel—chloroform as eluant) and was crystallized from chloroform/ether to give colorless needles of ethyl 5-methoxyimidazo-[1,2-a]-quinoline-2-carboxylate melting at 178°-179° C.

Analysis: $C_{15}H_{14}N_2O_3$. Calculated: %C 66.67; %H 5.22; %N 10.36; Found: C 66.41; H 5.29; N 10.31
I.R. (KBr Disc) 3120 cm$^{-1}$ (C—H$_1$ stretch); 1720 cm$^{-1}$ (Ester C=O);

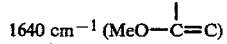
1640 cm$^{-1}$ (MeO—C=C)

EXAMPLE 4

THAM salt of 5-methoxyimidazo-[1,2-a]-quinoline-2-carboxylic acid 1.2 g of ethyl 5-methoxyimidazo-[1,2-a]-quinoline-2-carboxylate was mixed with 25 ml of methanol, 15 ml of water and 10 ml of 1 N sodium hydroxide solution. The mixture obtained was heated on a steam bath for 30 minutes, then was cooled and the methanol was evaporated under vacuum. The residual aqueous solution was acidified to a pH of 6 with phosphoric acid and the precipitate thus formed was filtered off, washed with water and then was dissolved in methanol. The solution obtained was decolorized with charcoal, evaporated to a reduced volume and then was cooled to obtain a fine white precipitate. The 507 mg of product were mixed with 254 mg of tris-(hydroxymethy)-aminomethane (THAM) in 10 ml of methanol and dissolution occured with warming. The solvent was evaporated from the solution under reduced pressure and the residue was triturated with acetone to obtain the THAM salt of 5-methoxyimidazo-[1,2-a]-quinoline-2-carboxylic acid as an off-white microcrystalline solid with a melting point of 90°-120° C.

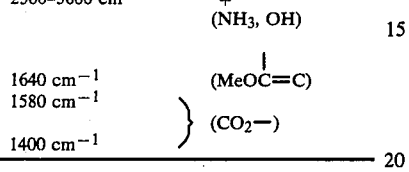

| I.R. (KBr Disc): 2300-3600 cm$^{-1}$ | (NH$_3$, $\overset{+}{\text{O}}$H) |
|---|---|
| 1640 cm$^{-1}$ | (MeO$\overset{|}{\text{C}}$=C) |
| 1580 cm$^{-1}$ | (CO$_2$—) |
| 1400 cm$^{-1}$ | |

EXAMPLE 5 ethyl 5-chloroimidazo-[1,2-a]-quinoline-2-carboxylate 4 g of ethyl bromopyruvate were added to a solution of 2 g of 2-amino-4-chloroquinoline [Hardman et al C.S., (1958), p. 614] in 40 ml of dimethoxyethane and the mixture obtained was allowed to stand at room temperature for 30 minutes. The quaternary salt thus precipitated was filtered off, washed with ether and then was dissolved in ethanol. The solution obtained was heated at reflux for 1 hour and then the ethanol was removed under vacuum. The residue was dissolved in chloroform and the solution was washed with dilute sodium carbonate solution and water, was decolorized with charcoal and the solvent was evaporated to leave a white solid. This solid was recrystallized from methanol to obtain fine white needles of ethyl 5-chloroimidazo-[1,2-a]-quinoline-2-carboxylate melting at 169°-170° C.

Analysis: C$_{14}$H$_{11}$N$_2$O$_2$Cl. Calculated: %C 61.21; %H 4.04; %Cl 12.90; %N 10.20; Found: C 61.16; H 4.02; Cl 12.97; N 10.28 I.R. (KBr Disc): 3140 cm$^{-1}$ (C-H$_1$ stretch 1705 cm$^{-1}$ (Ester C=O)

EXAMPLE 6

5-chloroimidazo-[1,2-a]-quinoline-2-carboxylic acid hydrochloride 820 mg of ethyl 5-chloroimidazo-[1,2-a]-quinoline-2-carboxylate were dissolved in 50 ml of ethanol and 6.6 ml of 0.5 N sodium hydroxide solution were added to the solution obtained. The resultant mixture was refluxed for 1 hour, then was cooled to room temperature and acidified to a pH of ~1 by addition of concentrated hydrochloric acid. The solvent was removed under vacuum and the residue was dissolved in methanol. The solution formed was filtered and the filtrate was reduced in volume under vacuum and then was cooled to obtain off-white crystals of 5-chloroimidazo-[1,2-a]-quinoline-2-carboxylic acid hydrochloride melting at 263°-265° C. (decomposition).

Analysis: C$_{12}$H$_8$Cl$_2$N$_2$O$_2$. Calculated: %C 50.91; %H 2.85; %Cl 25.04; %N 9.89; Found: C 50.80; H 2.87; Cl 25.25; N 9.96

I.R. (KBr Disc): 3135 cm$^{-1}$ (C—H$_1$ stretch); 2360-3000 cm$^{-1}$ (CO$_2$H, N$^+$H); 1735 cm$^{-1}$ (acid C=O).

EXAMPLE 7 ethyl 5-isopropoxyimidazo-[1,2-a]-quinoline-2-carboxylate 2.8 g of 2-amino-4-isopropoxyquinoline were dissolved in 50 ml of dimethoxyethane and 4 g of ethyl bromopyruvate were added thereto. The mixture obtained was allowed to stand at room temperature for 1 hour and then was reduced in volume under vacuum. 50 ml of ethanol were added thereto and the resultant mixture was refluxed for 90 minutes. The ethanol was evaporated off under vacuum and the residue was dissolved in 100 ml of 2 N HCl. The acid solution thus obtained was washed with 50 ml of ethyl acetate and then was made alkaline with sodium carbonate. The mixture was extracted three times with 50 ml of chloroform and the combined chloroform extracts were washed with 100 ml of water, dried over MgSO$_4$ and then was evaporated to dryness under reduced pressure to obtain an orange oil. The oil was purified by column chromatography (silica gel-chloroform as eluant) and then was crystallized from diethyl ether to obtain colorless needles of ethyl 5-isopropoxyimidazo-[1,2-a]-quinoline-2-carboxylate melting at 127°-129° C.

I.R. (KBr Disc): 3140 cm$^{-1}$ (C-H, stretch); 1713 cm$^{-1}$ (Ester C=O); 1640 cm$^{-1}$ (C=C—OCHMe$_2$)

Analysis: C$_{17}$H$_{18}$N$_2$O$_3$. Calculated: %C 68.44; %H 6.08; %N 9.39; Found: C 68.32; H 6.07; N 9.45

EXAMPLE 8

5-isopropoxyimidazo-[1,2-a]-quinoline-2-carboxylic acid hydrochloride 920 mg of ethyl 5-isopropoxyimidazo-[1,2-a]-quinoline-2-carboxylate were mixed with 20 ml of ethanol and 8 ml of 0.5 N sodium hydroxide solution. The mixture obtained was heated on a steam bath for 30 minutes and then was evaporated to dryness under vacuum. The residue was redissolved in 10 ml of methanol and the solution was acidified with HCl in ether. The resultant solution was decolorized with charcoal and then was evaporated to dryness. The residue was triturated with acetone to obtain colorless crystals of 5-isopropoxyimidazo-[1,2-a]-quinoline-2-carboxylic acid hydrochloride melting at 254°-7° C. (decomp.)

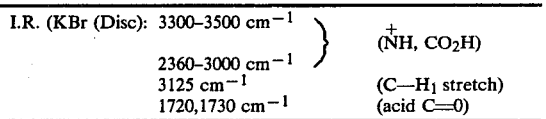

| I.R. (KBr (Disc): 3300-3500 cm$^{-1}$ | ($\overset{+}{\text{N}}$H, CO$_2$H) |
|---|---|
| 2360-3000 cm$^{-1}$ | |
| 3125 cm$^{-1}$ | (C—H$_1$ stretch) |
| 1720,1730 cm$^{-1}$ | (acid C=O) |

Analysis: C$_{15}$H$_{15}$ClN$_2$O$_3$. Calculated: %C 58.74; %H 4.93; %Cl 11.56; %N 9.13

EXAMPLE 9 ethyl 8-chloroimidazo-[1,2-a]-quinoline-2-carboxylate 2.0 g of 2-amino-7-chloroquinoline [Chem. Abs., Vol. 79, p. 92024t] were dissolved in 40 ml of dimethoxyethane and then a mixture of 2.5 g of ethyl bromopyruvate and 0.5 g of propylene oxide in 5 ml of dimethoxyethane was added thereto. The mixture obtained was allowed to stand at room temperature for 1 hour and the quaternary salt thus precipitated was filtered off, washed with ether and then was dissolved in 50 ml of ethanol. The solution was refluxed for 1 hour and on subsequent cooling in ice, the solution precipitated ethyl 8- chlorimidazo-[1,2-a]-quinoline-2-carboxylate hydrobromide as pale lemon hygroscopic crystals. This salt was partitioned between 50 ml of dilute sodium carbonate solution and 100 ml of chloroform and the organic solution was separated, washed with 50 ml of water, dried over MgSO$_4$ and was evaporated to dryness under reduced pressure. The residue was crystallized from chloroform/diethyl ether to give colorless crystals of ethyl 8-chloroimidazo-[1,2-a]-quinoline-2-carboxylate melting at 221°–222° C.

I.R. (KBr Disc): 3140 cm$^{-1}$ (C—H$_1$ stretch) 1715 cm$^{-1}$ (Ester C=O)

Analysis: C$_{14}$H$_{11}$Cl N$_2$O$_2$. Calculated: %C 61.21; %H 4.04; %Cl 12.90; %N 10.20; Found: C 61.08; H 4.09; Cl 13.10; N 10.21

EXAMPLE 10 sodium 8-chloroimidazo-[1,2-a]-quinoline-2-carboxylate 1.37 g of ethyl 8-chloroimidazo-[1,2-a]-quinoline-2-carboxylate hydrobromide were suspended in 50 ml of ethanol and 7.7 ml of 1 N sodium hydroxide were added thereto. The mixture obtained was heated on a steam bath for 30 minutes and sodium 8-chloroimidazo-[1,2-a]-quinoline-2-carboxylate precipitated as a white solid melting at >300° C.

| I.R. (KBr Disc): | 3170 cm$^{-1}$ | (C—H$_1$ stretch) |
|---|---|---|
| | 1620 cm$^{-1}$ | } (CO$_2$—) |
| | 1395 cm$^{-1}$ | |

Analysis: C$_{12}$H$_6$ClN$_2$O$_2$Na. Calculated: %C 53.65; %H 2.25; %Cl 13.20; %N 10.42

EXAMPLE 11 ethyl 5,8-dimethoxyimidazo-[1,2-a]-quinoline-2-carboxylate 1.5 g of 2-amino-4,7-dimethoxyquinoline were dissolved in 30 ml of dimethoxyethane and then 1.5 g of ethyl bromopyruvate were added thereto followed by 700 mg of triethylamine. The mixture obtained was allowed to stand at room temperature for 2 hours, and the solvent was evaporated under vacuum. The residue was dissolved in 100 ml of chloroform and the solution obtained was washed twice with 50 ml of water, dried over MgSO$_4$ and was evaporated to dryness under reduced pressure. The residue was purified by column chromatography (silica gel-ethyl acetate then chloroform/ethyl acetate as eluant) and was crystallized from diethyl ether to obtain ethyl 5,8-dimethoxyimidazo-1[1,2-a]-quinoline-2-carboxylate melting at 195°–197° C.

I.R. (KBr Disc): 3140 cm$^{-1}$ (C—H$_1$ stretch) 1720 cm$^{-1}$ (Ester C=O) 1635 cm$^{-1}$ (C=C—OMe)

Analysis: C$_{16}$H$_{16}$N$_2$O$_4$. Calculated: %C 63.99; %H 5.37; %N 9.33; Found: C 63.76; H 5.61; N 9.05

EXAMPLE 12

5,8-dimethoxyimidazo-[1,2-a]-quinoline-2-carboxylic acid

A mixture of 1 g of ethyl 5,8-dimethoxyimidazo-[1,2-a]-quinoline-2-carboxylate in a mixture of 10 ml of methanol and a 5% sodium carbonate solution was refluxed for 1 hour, and the resultant solution was acidified with dilute hydrochloric acid. The precipitate of 5,8-dimethoxyimidazo-[1,2-a]-quinoline-2-carboxylic acid thus formed was filtered off and was suspended in 10 ml of methanol. The mixture was acidified with HCl/methanol to obtain a clear solution from which the acid crystallized upon addition of diethyl ether to obtain the said acid melting at 248°–250° C.

| I.R. (KBr Disc): | 3300–3600 cm$^{-1}$ | } $^+$NH, CO$_2$H |
|---|---|---|
| | 2400–3000 cm$^{-1}$ | |
| | 3160 cm$^{-1}$ | (C—H$_1$ stretch) |
| | 1735 cm$^{-1}$ weak | (CO$_2$H) |
| | 1630 cm$^{-1}$ broad | (CO$_2$—) |

I.R. Spectrum suggests that the compound exists partially in the zwitterionic form.

Analysis: C$_{14}$H$_{12}$N$_2$O$_4$. Calculated: %C 61.76; %H 4.44; %N 10.29; Found: C 61.65; H 4.41; N 10.03

EXAMPLE 13 ethyl 8-methoxy-5-isopropoxyimidazo-[1,2-a]-quinoline-2-carboxylate 1.5 g of 2-amino-7-methoxy-4-isopropoxy-quinoline and 1.5 g of ethyl bromopyruvate were reacted by the method of Example 11 to obtain ethyl 8-methoxy-5-isopropoxyimidazo-[1,2-a]-quinoline-2-carboxylate melting at 117°–118° C.

I.R. (KBr Disc): 3140 cm$^{-1}$ (C—H$_1$ stretch); 1713 cm$^{-1}$ (Ester C=O); 1634 cm$^{-1}$ (C=C—OCHMe$_2$)

Analysis: C$_{18}$H$_{20}$N$_2$O$_4$. Calculated: %C 65.84; %H 6.14; %N 8.53; Found: C 65.43; H 6.19; N 8.25

EXAMPLE 14

8-methoxy-5-isopropoxyimidazo-[1,2-a]-quinoline-2-carboxylic acid 8-methoxy-5-isopropoxyimidazo-[1,2-a]-quinoline-2-carboxylic acid was prepared from ethyl 8-methoxy-5-isopropoxyimidazo-[1,2-a]-quinoline-2-carboxylate by the method of Example 12 to obtain the product melting at 259°–261° C.

| I.R. (KBr Disc): | 3200–3600 cm$^{-1}$ | } ($\overset{+}{N}$H H$_2$O) |
|---|---|---|
| | 2400–3000 cm$^{-1}$ | |
| | 3135 cm$^{-1}$ | (C—H$_1$ stretch) |
| | 1610 cm$^{-1}$ | (CO$_2$—) |

Analysis: C$_{16}$H$_{16}$N$_2$O$_4$ ½ H$_2$O. Calculated: %C 62.13; %H 5.23; %N 9.01; Found: C 62.13; H 5.54; N 9.06

No carboxylic acid carbonyl was visible—compound must exist entirely in the zwitterionic form.

EXAMPLE 15 ethyl 5-chloro-8-methoxyimidazo-[1,2-a]-quinoline-2-carboxylate 1.3 g of 2-amino-4-chloro-7-methoxyquinoline were dissolved in 20 ml of dimethoxyethane and 1.3 g of ethyl bromopyruvate were added thereto. The mixture was stirred at room temperature for 2 hours and the crystalline intermediate thus formed was filtered off, washed with ether and then was dissolved in 20 ml of ethanol. The resultant solution was refluxed for 3 hours and ethyl 5-chloro-8-methoxyimidazo-[1,2-a]-quinoline-2-carboxylate melting at 215°–216° C. was isolated by the procedure of Example 9.

I.R. (KBr Disc): 3140 cm$^{-1}$ (C—H$_1$ stretch); 1720 cm$^{-1}$ (Ester C=O)

Analysis: $C_{15}H_{13}ClN_2O_3$. Calculated: %C 59.12; %H 4.30; %Cl 11.63; %N 9.19; Found: C 59.13; H 4.25; Cl 11.85; N 9.14

2-amino-4-chloro-7-methoxyquinoline used as a starting material was prepared from the corresponding 4-hydroxyquinoline with phosphorus oxychloride under reflux by the method of Hardman et al [J. Chem. Soc. (1958), p. 614].

EXAMPLE 16

5-chloro-8-methoxyimidazo-[1,2-a]-quinoline-2-carboxylic acid hydrochloride 800 mg of ethyl 5-chloro-8-methoxyimidazo-[1,2-a]-quinoline-2-carboxylate were mixed with 10 ml of methanol and 20 ml of 1 N sodium hydroxide solution. The mixture obtained was refluxed for 1 hour and the solid sodium salt which separated out was filtered off and then was dissolved in 20 ml of water. The solution was acidified with concentrated hydrochloric acid to obtain a white precipitate of 5-chloro-8-methoxyimidazo-[1,2-a]-quinoline-2-carboxylic acid. The precipitate was filtered off and was suspended in 10 ml of methanol and the suspension was acidified with HCl/methanol to obtain a clear solution to which diethyl ether was subsequently added to give 5-chloro-8-methoxyimidazo-[1,2-a]-quinoline-2-carboxylic acid hydrochloride melting at 284°–286° C.

I.R. (KBr Disc): 3130 cm$^{-1}$ (C—H$_1$ stretch); 2400–3300 cm$^{-1}$ (CO$_2$H); 1740 cm$^{-1}$ (acid C=O)

EXAMPLE 17 ethyl 8-chloro-5-isopropoxyimidazo-[1,2-a]-quinoline-2-carboxylate 1.9 g of 2-amino-7-chloro-4-isopropoxyquinoline were dissolved in 20 ml of dimethoxyethane and 1.9 g of ethyl bromopyruvate were added thereto followed by 800 mg of triethylamine. The mixture obtained was stirred at room temperature for 4 hours and then the solvent was evaporated under vacuum. The residue was dissolved in 100 ml of chloroform and the solution was dried over MgSO$_4$ and was evaporated to dryness under vacuum. The residue was dissolved in 25 ml of ethanol and the solution was refluxed for 3 hours and then the solvent was removed under vacuum. The residue was purified by column chromatography (silica gel-chloroform/methanol eluant) and then was crystallized from diethyl ether to obtain pale cream needles of ethyl 8-chloro-5-isopropoxyimidazo-[1,2-a]-quinoline-2-carboxylate melting at 187°–189° C.

I.R. (KBr Disc): 3140 cm$^{-1}$ (C—H$_1$ stretch); 1710 cm$^{-1}$ (Ester C=O); 1633 cm$^{-1}$ (C=C—OCHMe$_2$)

Analysis: $C_{17}H_{17}ClN_2O_3$. Calculated: %C 61.36; %H 5.15; %Cl 10.65; %N 8.42; Found: C 61.57; H 5.15; Cl 10.90; N 8.35

2-amino-7-chloro-4-isopropoxyquinoline, used as a starting material, was prepared from the corresponding 2-amino-7-chloro-4-hydroxyquinoline with an isopropyl p-toluenesulfonate at 120°–140° C. by the method of Grout et al [J. Chem. Soc. Perkin Vol. 1 (1973), p. 1314].

EXAMPLE 18

8-chloro-5-isopropoxyimidazo-[1,2-a]-quinoline-2-carboxylic acid 750 mg of ethyl 8-chloro-5-isopropoxyimidazo-[1,2-a]-quinoline-2-carboxylate were dissolved in 50 ml of ethanol and 3 ml of 1 N sodium hydroxide solution were added thereto. The mixture obtained was refluxed for 1 hour, was neutralized while hot by addition of 1.5 ml of 2 N hydrochloric acid and then was cooled slowly to give white crystals of 8-chloro-5-isopropxyimidazo-[1,2-a]-quinoline-2-carboxylic acid melting at 283°–285° C.

I.R. (KBr Disc.); 3100 cm$^{-1}$ (C—H$_1$ stretch); 1720 cm$^{-1}$ (Acid C=O); 1635 cm$^{-1}$ (C=C—OCHMe$_2$)

Analysis: $C_{15}H_{13}ClN_2O_3$. Calculated: %C 59.12; %H 4.30; %Cl 11.63; %N 9.19; Found: C 59.04; H 4.30; Cl 11.62; N 9.15

EXAMPLE 19 ethyl 8-methoxyimidazo-[1,2-a]-quinoline-2-carboxylate 50 ml of 2-amino-7-methoxyquinoline [C.A., Vol. 79, p. 92024t] were dissolved in 50 ml of dimethoxyethane and then a mixture of 3 g of ethyl bromopyruvate and 1 g of propylene oxide in 5 ml of dimethoxyethane was added thereto. The mixture was allowed to stand at 5° C. for 16 hours and the intermediate quaternary salt thus precipitated was filtered off, washed with diethyl ether and then was dissolved in 50 ml of ethanol. The solution was refluxed for 1 hour and then was reduced in volume under vacuum. Diethyl ether was subsequently added thereto to precipitate ethyl 8-methoxyimidazo-[1,2-a]-quinoline-2-carboxylate hydrobromide which was filtered off and was washed with diethyl ether. The hydrobromide was partitioned between 50 ml of dilute sodium carbonate solution and 100 ml of chloroform and the organic solution was separated, washed with 50 ml of water, was dried over MgSO$_4$ and was evaporated to dryness under reduced pressure. The residue was crystallized from diethyl ether to obtain buff crystals of ethyl 8-methoxyimidazo-[1,2-a]-quinoline-2-carboxylate melting at 146°–148° C.

I.R. (KBr Disc): 3140 cm$^{-1}$ (C—H$_1$ stretch); 1700 cm$^{-1}$ (Ester C=O)

Analysis: $C_{15}H_{14}N_2O_3$. Calculated: %C 66.66; % 5.22; %N 10.36; Found: C, 66.39; 5.24; N 10.30

EXAMPLE 20

8-methoxyimidazo-[1,2-a]-quinoline-2-carboxylic acid 1.35 g of ethyl 8-methoxyimidazo-[1,2-a]-quinoline-2-carboxylate were dissolved in 60 ml of ethanol and 2.5 ml of 2 N sodium hydroxide were added thereto. The mixture was refluxed for 1 hour whereupon a colorless gel was produced and after 3 ml of 2 N hydrochloric acid were added, and the mixture was refluxed for another 60 minutes and then was allowed to cool to room temperature. The cream precipitate thus formed was filtered off and was recrystallized from glacial acetic acid and then was washed with methanol to obtain off-white crystals of 8-methoxyimidazo-[1,2-a]-quinoline-2-carboxylic acid melting at 272°–273° C.

I.R. (KBr Disc): 3130 cm$^{-1}$ (C—H$_1$ stretch); 1750 cm$^{-1}$ (Acid C=O)

Analysis: $C_{13}H_{10}N_2O_3$. Calculated: %C 64.46; %H 4.16; %N 11.56; Found: C 64.16; H 4.19; N 11.45

EXAMPLE 21 ethyl 5,8-dichloroimidazo-[1,2-a]-quinoline-2-carboxylate 1.8 g of 2-amino-4,7-dichloroquinoline [Hardman and Partridge J.C.S. (1958) p. 641] were reacted with 2.1 g of ethyl bromopyruvate in 60 ml of dimethoxyethane in the presence of 0.7 g of propylene oxide by the method of Example 9 to obtain ethyl 5,8-dichloroimidazo-[1,2-a]-quinoline-2-carboxylate as fine colorless needles melting at 229°–230° C.

I.R. (KBr Disc): 3140 cm$^{-1}$ (C—H$_1$ stretch) 1712 cm$^{-1}$ (Ester C=O)

Analysis: $C_{14}H_{10}Cl_2N_2O_2$ Calculated: %C 54.39; %H 3.26; %Cl 22.94; %N 9.06; Found: C 54.21; H 3.24; Cl 23.16; N 9.11

EXAMPLE 22

5,8-dichloroimidazo-[1,2-a]-quinoline-2-carboxylic acid 1.24 g of ethyl 5,8-dichloroimidazo-[1,2-a]-quinoline-2-carboxylate were hydrolyzed with 3 ml of 2 N sodium hydroxide solution in 120 ml of 50—50 mixture of dimethoxyethane and ethanol. The resultant mixture was neutralized with 3.3 ml of 2 N hydrochloric acid by the method of Example 20 to obtain fine off-white crystals of 5,8-dichloroimidazo-[1,2-a]-quinoline-2-carboxylic acid melting at ≈305° C. (decomp).

I.R. (KBr Disc): 3135 cm$^{-1}$ (C—H$_1$ stretch) 1740 cm$^{-1}$ (Acid C=O)

Analysis: $C_{12}H_6Cl_2N_2O_2$. Calculated: %C 51.27; %H 2.15; %Cl 25.22; %N 9.96; Found: C 51.18; H 2.31; Cl 24.91; N 9.84

EXAMPLE 23 ethyl 7-chlorimidazo-[1,2-a]-quinoline-2-carboxylate 800 mg of 2-amino-6-chloroquinoline, 1.0 g of ethyl bromopyruvate and 200 mg of propylene oxide in 15 ml of dimethoxyethane were reacted as in Example 9 to obtain after recrystallization from chloroform/diethyl ether colorless crystals of ethyl 7-chloroimidazo-[1,2-a]-quinoline-2-carboxylate melting at 194°–195° C.

I.R. (KBr Disc): 3130 cm$^{-1}$ (C—H$_1$ stretch) 1710 cm$^{-1}$ (Ester C=O)

Analysis: $C_{14}H_{11}ClN_2O_2$. Calculated: %C 61.21; %H 4.04; %Cl 12.90; %N 10.20; Found: C 61.04; H 4.00; Cl 13.20; N 10.21

EXAMPLE 24

7-chloroimidazo-[1,2-a]-quinoline-2-carboxylic acid monohydrate 820 mg of ethyl 7-chloroimidazo-[1,2-a]-quinoline-2-carboxylate in 25 ml of ethanol and 1 N sodium hydroxide solution was added thereto. The mixture obtained was heated on a steam bath for 30 minutes and then was diluted with 50 ml of water. The mixture was neutralized with 3.5 ml of 2 N hydrochloric acid and then cooled to obtain pale cream crystals of 7-chloroimidazo-[1,2-a]-quinoline-2-carboxylic acid monohydrate melting at 278°–279° C. The I.R. spectrum suggests that the compound exists at least partially in the zwitterionic form.

| I.R. (KBr Disc): | 3300–3650 cm$^{-1}$ | NH$^+$, CO$_2$H, OH |
|---|---|---|
| | 2200–3000 cm$^{-1}$ | |
| | 1800–2000 cm$^{-1}$ | |
| | 3140 cm$^{-1}$ | (C—H$_1$ stretch) |
| | 1735 cm$^{-1}$ | (weak) (Acid C=O) |

Analysis: $C_{12}H_7ClN_2O_2 \cdot H_2O$. Calculated: %C 54.46; %H 3.43; %Cl 13.39; %N 10.58; Found: C 54.20; H 3.22; Cl 13.43; N 10.47

EXAMPLE 25 ethyl 5-bromoimidazo-[1,2-a]-quinoline-2-carboxylate 1 g of 2-amino-4-bromoquinoline was dissolved in 20 ml of dimethoxyethane and a mixture of 1.5 g of ethyl bromopyruvate and 0.5 g of propylene oxide was added thereto. The solution was allowed to stand at room temperature for 1 hour and the quaternary salt thus precipitated was filtered off, was washed with ether and then was dissolved in 20 ml of ethanol. The solution was refluxed for 1 hour, cooled and then was evaporated to dryness under vacuum. The residue was partitioned between 50 ml of chloroform and 50 ml of 2 N sodium carbonate and the organic extract was washed with 50 ml of water, was dried over MgSO$_4$, and was reduced in volume under vacuum. Then, ether was added thereto to give cream needles of ethyl 5-bromoimidazo-[1,2-a]-quinoline-2-carboxylate melting at 205°–207° C.

I.R. (KBr Disc): 3150 cm$^{-1}$ (C—H$_1$ stretch) 1727 cm$^{-1}$ (Ester C=O)

Analysis: $C_{14}H_{11}BrN_2O_2$. Calculated: %C 52.69; %H 3.48; %Br 25.04; %N 8.78; Found: C 52.43; H 3.51; Br 24.81; N 8.66

EXAMPLE 26

5-bromoimidazo-[1,2-a]-quinoline-2-carboxylic acid 1.28 g of ethyl 5-bromoimidazo-[1,2-a]-quinoline-2-carboxylate were heated on a steam bath with 5 ml of 1 N sodium hydroxide solution in 20 ml of water and 50 ml of ethanol until a clear solution was obtained (approx. 15 mins). 5 ml of 1 N hydrochloric acid were then added thereto and the solution was allowed to cool slowly to room temperature. The pale green crystals thus formed were filtered off and were washed with methanol. The mother liquors were reduced in volume and cooled to give a second crop. The two crops were combined in 50 ml of chloroform and 50 methanol and the solution obtained was decolorized with charcoal. The solution was reduced in volume under vacuum and the residue was cooled in ice to give colorless plates of 5-bromoimidazo-[1,2-a]-quinoline-2-carboxylic acid melting at 288°–90° C. (decomp).

I.R. (KBr Disc): 3140 cm$^{-1}$ (C—H$_1$ stretch) 1715 cm$^{-1}$ (Acid C=O)

Analysis: $C_{12}H_7BrN_2O_2 \cdot CH_3OH$. Calculated: %C 48.32; %H 3.43; %Br 24.73; %N 8.67; Found: C 48.37; H 3.23; Br 24.93; N 8.63

EXAMPLE 27 ethyl 7-methoxyimidazo-[1,2-a]-quinoline-2-carboxylate 3.2 g of 6-methoxyquinoline were dissolved in 25 ml of dimethoxyethane and then a mixture of 4.2 g of ethyl bromopyruvate and 1.2 g of propylene oxide were added. The mixture was allowed to stand at room temperature overnight and then 50 ml of ether were added and the supernatant liquid decanted off. The residual oil was dissolved in 100 ml of glacial acetic acid and 5 g of hydroxylamine hydrochloride were added. The mixture was heated to reflux for 24 hours and the mixture was poured into 400 ml of water. The solution was made alkaline with sodium carbonate and was extracted with ethyl acetate. The extract was washed with water, dried over magnesium sulfate and evaporated to dryness under vacuum. The residue was chromatographed over silica with ether as eluent and the purified product was crystallized by trituration with ether to give ethyl 7- methoxyimidazo-[1,2-a]-quinoline-2-carboxylate as colorless needles melting at 119°-121° C.

I.R. (KBr Disc): 3135 cm$^{-1}$ (C—H$_1$ stretch); 1720 cm$^{-1}$ (Ester C=O)

Analysis: C$_{15}$H$_{14}$N$_2$O$_3$. Calculated: %C 66.66; %H 5.22; %N 10.36; Found: C 66.45; H 5.28; N 10.33

EXAMPLE 28

7-methoxyimidazo-[1,2-a]-quinoline-2-carboxylic acid 840 mg of ethyl 7-methoxyimidazo-[1,2-a]-quinoline-2-carboxylate were suspended in a mixture of 100 ml of water and 150 ml of ethanol and 3.5 ml of N sodium hydroxide solution were added. The mixture was heated on a steam bath for 30 minutes and the resulting solution was decolorized with charcoal, filtered and acidified with 3.7 ml of N hydrochloric acid. The mixture was cooled in ice to obtain colorless crystals of 7-methoxyimidazo-[1,2-a]-quinoline-2-carboxylic acid melting at 265°-266° C.

I.R. (KBr Disc): 3130 cm$^{-1}$ (C—H$_1$ stretch) 2400-3000 cm$^{-1}$ (Acid —OH) 1690 cm$^{-1}$ (Acid C=O)

Analysis: C$_{13}$H$_{10}$N$_2$O$_3$. Calculated: %C 64.46; %H 4.16; %N 11.56; Found: C 64.16; H 4.19; N 11.48

EXAMPLE 29 ethyl 6-chloroimidazo-[1,2-a]-quinoline-2-carboxylate 140 mg of 2-amino-5-chloroquinoline were dissolved in 2.5 ml of dimethoxyethane and then a mixture of 170 mg of ethyl bromopyruvate and 30 mg of propylene oxide was added. The mixture was stirred at room temperature for 2 hours and 2 ml of ether were added. Then, the mixture was cooled in ice and the precipitated quaternary salt was filtered off, was dissolved in 5 ml of ethanol and the solution was heated at reflux for 2 hours. Then, the solvent was removed under vacuum and the residue was partitioned between sodium bicarbonate solution and chloroform. The chloroform solution was dried over magnesium sulfate and was evaporated to dryness. The residue was chromatographed over silica with chloroform as eluent and the purified product was recrystallized from ethyl acetate/petroleum ether to obtain colorless needles of ethyl 6-chloroimidazo-[1,2-a]-quinoline-2-carboxylate melting at 193°-194° C.

I.R. (KBr Disc): 3145 cm$^{-1}$ (C—H$_1$ stretch) 1707 cm$^{-1}$ (Ester C=O)

Analysis: C$_{14}$H$_{11}$N$_2$Cl O$_2$. Calculated: %C 61.21; %H 4.04; %N 10.20; Found: C 61.13; H 4.05; N 10.07

EXAMPLE 30

6-chloroimidazo-[1,2-a]-quinoline-2-carboxylic acid 100 mg of ethyl 6-chloroimidazo-[1,2-a]-quinoline-2-carboxylate were suspended in a mixture of 4.5 ml of ethanol and 2 ml of water and then 0.5 ml of N sodium hydroxide solution was added. The mixture was heated on a steam bath for 4 hours and the resulting solution was filtered then acidified with 0.5 ml of N hydrochloric acid and cooled to give colorless crystals of 6-chloroimidazo-[1,2-a]-quinoline-2-carboxylic acid monohydrate melting at 288°-289° C.

I.R. (KBr Disc): 3200-3700 cm$^{-1}$ (H$_2$O) 3140 cm$^{-1}$ (C—H$_1$ stretch) 2300-3000 cm$^{-1}$ (Acid —OH) 1742,1710 cm$^{-1}$ (Acid C=O)

Analysis: C$_{12}$H$_7$N$_2$ClO$_2$.H$_2$O. Calculated: %C 56.56; %H 3.56; %N 11.00; Found: C 56.34; H 3.24; N 10.84

EXAMPLE 31 ethyl 8-bromo-5-chloroimidazo-[1,2-a]-quinoline-2-carboxylate 1 g of 2-amino-7-bromo-4-chloroquinoline was suspended in 10 ml of dimethoxyethane and then a solution of 1 g of ethyl bromopyruvate and 300 mg of propylene oxide in 10 ml of dimethoxyethane was added. The mixture was stirred at room temperature for 2 days and 300 mg of ethyl bromopyruvate were then added. Stirring was continued for a further day and the precipitated quaternary salt was filtered off, washed with ether and then was suspended in 20 ml of ethanol. The mixture was heated at reflux for 2 hours and the solvent was removed under vacuum. The residue was partitioned between CHCl$_3$/Na$_2$CO$_3$ solution and the organic solution was dried over MgSO$_4$ and the solvent was removed to leave a cream solid. This was purified by chromatography over silica with 5% methanol in chloroform as eluent and the product was crystallized from chloroform/ether to obtain pale cream needles of ethyl 8-bromo-5-chloroimidazo-[1,2-a]-quinoline-2-carboxylate melting at 206° to 207° C.

I.R. (KBr Disc): 3145 cm$^{-1}$ (C—H$_1$ stretch) 1718 cm$^{-1}$ (Ester C=O)

Analysis: C$_{14}$H$_{10}$N$_2$BrClO$_2$. Calculated: %C 47.56; %H 2.85; %N 7.92; Found: C 47.41; H 2.87; N 7.82

EXAMPLE 32

8-bromo-5-chloroimidazo-[1,2-a]-quinoline-2-carboxylic acid 400 mg of ethyl 8-bromo-5-chloroimidazo-[1,2-a]-quinoline-2-carboxylate were suspended in 200 ml of 50% aqueous ethanol and 4 ml of N sodium hydroxide solution were added. The mixture was heated on a steam bath for 1 hour and the resulting solution was filtered, then acidified with 4.4 ml of N hydrochloric acid. The mixture was cooled in ice to obtain cream needles of 8-bromo-5-chloroimidazo-[1,2-a]-quinoline-2-carboxylic acid monohydrate melting at >300° C.

I.R. (KBr Disc): 3300-3600 cm$^{-1}$ (H$_2$O); 3145 cm$^{-1}$ (C—H$_1$ stretch); 2400-3000 cm$^{-1}$ (Acid —OH); 1746 cm$^{-1}$ (Acid C=O)

Analysis: C$_{12}$H$_6$N$_2$BrClO$_2$.H$_2$O. Calculated: %C 41.95; %H 2.35; %N 8.15; %Br 23.26; %Cl 10.32; Found: C 42.08; H 2.30; N 8.11; Br 23.12; Cl 10.19

EXAMPLE 33

(2,2-dimethyl-1,3-dioxolan-4-yl)-methyl imidazo-[1,2-a]-quinoline-2-carboxylate 5 g of imidazo-[1,2-a]-quinoline-2-carboxylic acid were added to 90 ml of thionyl chloride containing 10 drops of DMF and the mixture was heated at reflux for 3 hours. Excess thionyl chloride was removed under vacuum and 50 ml of dry toluene were added. The solution was again evaporated to dryness and the residue was triturated with dry ether. The yellow acrid solid, a mixture of the acid chloride and acid anhydride, was filtered off and this 3 g of solid were added to a solution of 1.5 g of glycerol acetonide and triethylamine in 100 ml of dichloroethane. The mixture was refluxed overnight and the resulting suspension was filtered. The filtrate was evaporated and the residue was chromatographed over silica with chloroform as eluent. The more polar material was crystallized from chloroform/ether and was identified as (2,2-dimethyl-1,3-dioxolan-4-yl)-methyl imidazo-[1,2-a]-quinoline-2-carboxylate melting at 156°–158° C.

I.R. (KBr Disc): 3145 cm$^{-1}$ (C—H$_1$ stretch); 1710 cm$^{-1}$ (Ester C=O)

Analysis: $C_{18}H_{18}N_2O_4$. Calculated: %C 66.25; %H 5.56; %N 8.58; Found: C 66.21; H 5.58; N 8.56

EXAMPLE 34

2,3-dihydroxypropyl imidazo-[1,2-a]-quinoline-2-carboxylate 0.45 g of (2,2-dimethyl-1,3-dioxolan-4-yl)-methyl imidazo-[1,2-a]-quinoline-2-carboxylate was suspended in 90 ml of water containing 0.48 g of citric acid monohydrate and the mixture was refluxed for 4 hours. Saturated sodium bicarbonate solution was then added and the precipitate was filtered off, washed with water and dried under vacuum. This solid was crystallized from chloroform/ether to give 2,3-dihydroxypropyl imidazo-[1,2-]-quinoline-2-carboxylate melting at 217°–220° C.

I.R. (KBr Disc): 3000–3600 cm$^{-1}$ (OH) 3145 cm$^{-1}$ (C—H$_1$ stretch) 1720 cm$^{-1}$ (Ester C=O)

Analysis: $C_{15}H_{14}N_2O_4$. Calculated: %C 62.93; %H 4.93; %N 9.78; Found: C 62.65; H 4.97; N 9.74

EXAMPLE 35

2-piperidinoethyl imidazo-[1,2-a]-quinoline-2-carboxylate 0.85 g of imidazo-[1,2-a]-quinoline-2-carboxylic acid was dissolved in 25 ml of dry DMF and then 0.72 g of carbonyl diimidazole was added with stirring. The temperature was raised to 80° C. for 15 minutes and 0.57 g of (2-hydroxyethyl) piperidine was then added. The mixture was stirred at 100° C. for 3 hours and was cooled to room temperature and filtered. Then, 50 ml of water were added dropwise to the filtrate and the precipitate was filtered off, washed with water and dried under vacuum. This solid was crystallized from ethyl acetate/petroleum ether to obtain 2-piperidinoethyl imidazo-[1,2-a]-quinoline-2-carboxylate hemihydrate melting at 147°–150° C.

I.R. (KBr Disc): 3200–3600 cm$^{-1}$ (H$_2$O) 3145 cm$^{-1}$ (C—H$_1$ stretch) 1700 cm$^{-1}$ (Ester C=O)

Analysis: $C_{19}H_{21}N_3O_2 \cdot 1/2H_2O$. Calculated: %C 68.65; %H 6.67; %N 12.64; Found: C 68.57; H 6.38; N 12.74

EXAMPLE 36 imidazo-[1,2-a]-quinoline-2-carboxylic acid 2 g of ethylimidazo-[1,2-a]-quinoline-2-carboxylate were suspended in 40 ml of ethanol and 20 ml of water and 9 ml of N NaOH were added. The mixture was heated on a steam bath for 30 minutes and the hot solution was acidified with 9.5 ml of N hydrochloric acid. The mixture was cooled slowly to room temperature and then in ice to give colorless needles of imidazo-[1,2-a]-quinoline-2-carboxylic acid monohydrate melting at 234°–236° C. The I.R. spectrum suggested that the compound existed partially in the zwitterionic form.

| I.R. (KBr Disc): 3200–3750 cm$^{-1}$ | (H$_2$O, $\overset{+}{N}H$, Acid—OH) |
|---|---|
| 2100–3000 cm$^{-1}$ | |
| 3140 cm$^{-1}$ | (C—H$_1$ stretch) |
| 1710 cm$^{-1}$ | (weak) (Acid C=O) |

Analysis: $C_{12}H_8N_2O_2 \cdot H_2O$. Calculated: %C 62.60; %H 4.38; %N 12.17; Found: C 62.66; H 4.13; N 12.08

EXAMPLE 37

5-methoxyimidazo-[1,2-a]-quinoline-2-carboxylic acid 250 mg of ethyl 5-methoxyimidazo-[1,2-a]-quinoline-2-carboxylate in 20 ml of ethanol and 10 ml of water was hydrolyzed with 2 ml of N sodium hydroxide solution and was then acidified with 2.2 ml of N hydrochloric acid as in Example 36 to obtain 5-methoxyimidazo-[1,2-a]-quinoline-2-carboxylic acid as colorless needles melting at 244°–247° C. The I.R. spectrum indicated that the compound existed entirely in the zwitterionic form.

| I.R. (KBr Disc): 3200–3600 cm$^{-1}$ | $(\overset{+}{NH})$ |
|---|---|
| 2500–3000 cm$^{-1}$ | |
| 3130 cm$^{-1}$ | (C—H$_1$ stretch) |
| 1620 cm$^{-1}$ | (CO$_2$—) |

Analysis: $C_{13}H_{10}N_2O_3$. Calculated: %C 64.46; %H 4.16; %N 11.56; Found: C 64.33; H 4.11; N 11.56

EXAMPLE 38

8-chloroimidazo-[1,2-a]-quinoline-2-carboxylic acid 200 mg of ethyl 8-chloroimidazo-[1,2-a]-quinoline-2-carboxylate in 8 ml of ethanol and 2 ml of water were hydrolyzed with 1 ml of N sodium hydroxide solution. The mixture was acidified with 1.1 ml of N HCl as in Example 36 to obtain colorless needles of 8-chloroimidazo-[1,2-a]-quinoline-2-carboxylic acid melting at 288°–289° C.

I.R. (KBr (Disc): 3145 cm$^{-1}$ (C—H$_1$ stretch) 1740 cm$^{-1}$ (Acid C=O)

Analysis: $C_{12}H_7N_2ClO_2$. Calculated: %C 58.44; %H 2.86; %N 11.36; %Cl 14.37; Found: C 58.37; H 2.88; N 11.32; Cl 14.49

EXAMPLE 39

5-chloro-8-methoxyimidazo-[1,2-a]-quinoline-2-carboxylic acid 600 mg of ethyl 5-chloro-8-methoxyimidazo-[1,2-a]-quinoline-2-carboxylate were suspended in 100 ml of 50% aqueous ethanol and then 4.4 ml of N sodium hydroxide solution were added. The mixture was heated on a steam bath for 1 hour and the resulting solution was acidified with 4.4 ml of N hydrochloric acid and then was cooled to room temperature to obtain colorless crystals of 5-chloro-8-methoxy-imidazo-[1,2-a]-quinoline-2-carboxylic acid melting at 277°–278° C.

I.R. (KBr Disc): 3140 cm$^{-1}$ (C—H$_1$ stretch) 1745 cm$^{-1}$ (Acid C=O)

Analysis: $C_{13}H_9N_2ClO_3$. Calculated: %C 56.44; %H 3.28; %N 12.81; %Cl 10.12; Found: C 56.65; H 3.33; N 13.06; Cl 10.08

EXAMPLE 40

5-isopropoxyimidazo-[1,2-a]-quinoline-2-carboxylic acid 300 mg of 5-isopropoxyimidazo-[1,2a]-quinoline-2-carboxylic acid hydrochloride were dissolved in 20 ml of ethanol and 5 ml of water containing 2 ml of N sodium hydroxide solution and then 1 ml of N hydrochloric acid was added. The solution was reduced in volume under vacuum and the residue was triturated with water to obtain a white precipitate of 5-isopropoxyimidazo-[1,2-a]-quinoline-2-carboxylic acid monohydrate melting at 247°-249° C. The I.R. spectrum indicated that the compound existed in the zwitterionic form.

| I.R. (KBr Disc): 3200-3600 cm$^{-1}$ | } ($H_2O$, $\overset{+}{N}H$) |
|---|---|
| 2400-2800 cm$^{-1}$ | |
| 3110 cm$^{-1}$ | (C—$H_1$ stretch) |
| 1625 cm$^{-1}$ | ($CO_2$) |

Analysis: $C_{15}H_{14}N_2O_3 \cdot H_2O$. Calculated: %C 62.49; %H 5.59; %N 9.72; Found: C 62.55; H 5.57; N 9.75

EXAMPLE 41 ethyl 8-methoxyimidazo-[1,2-a]-quinoline-2-carboxylate 5 g of ethyl 5-chloro-8-methoxyimidazo-[1,2-a]-quinoline-2-carboxylate were suspended in 75 ml of ethanol and 75 ml of ethyl acetate and then 2.5 g of anhydrous sodium acetate and 250 mg of 5% palladium on charcoal were added. The mixture was hydrogenated at 50° C. under atmospheric pressure for 4 hours and the catalyst was filtered off. Then, the solvent was removed under vacuum and the residue was partitioned between chloroform and 2 N sodium carbonate solution. The organic solution was dried over magnesium sulfate and was reduced in volume under vacuum and ether was added to obtain pale cream crystals of ethyl 8-methoxyimidazo-[1,2-a]-quinoline-2-carboxylate melting at 152°-153° C.

EXAMPLE 42

Tablets were prepared containing 2 mg of 5,8-dichloroimidazo-[1,2-a]-quinoline-2-carboxylic acid and sufficient excipient of lactose, talc, starch and magnesium stearate for a tablet of 100 mg.

EXAMPLE 43

A metered dose aerosol dispenser was packed with the following ingredients per dose: 2 mg of 5-chloroimidazo-[1,2-a]-quinoline-2-carboxylic acid hydrochloride, 0.15 mg of an emulsifier and 50 mg of propellant.

PHARMACOLOGICAL STUDY

Passive cutaneous anaphylaxis (PCA) in rats

Cutaneous anaphylaxis can be induced in rats by intradermal (ID) sensitization with antiserum followed three days later by systemic challenge with antigen. Evans blue dye injected with the antigen is used as a marker to assess the severity of the local response. Antiallergic drugs inhibit this reaction. This method has been described by OVARY (1962) "Passitive Cutaneous Anaphylaxis in Allergology" Page 358-367 Ed. Brown: Pergamon Press:-male rats weighing 180-220 grams are used in groups of seven.

Preparation of Antigen for Sensitization (Alum precipitated ovalbumen).

1. Wash 120 grams of $Al(OH)_3$ gel in 140 ml of saline (use of a macerater facilitates mixing).

2. Centrifuge at 3,000 r.p.m. for about 10 minutes.

3. Resuspend the precipitate with 300 ml of albumen egg powder (1.3 mg/ml) in saline and allow to stand for 30 minutes.

4. Centrifuge at 3,000 r.p.m. for 10 minutes.

5. Weigh the wet precipitate and to each gram weight add 1 ml of saline. Store in refrigerator (Quantity sufficient for 60 rats for a 3 day sensitization program).

Preparation of Antiserum (anti-ovalbumen)

1 ml of the alum precipitated ovalbumen was injected subcutaneously into rats weighing 180-220 grams on days 0,2,4. The rats were bled on day 14 either by cardiac puncture or via the dorsal abdominal aorta. Equal quantities of serum from each animal were pooled and thoroughly mixed and 2 ml aliquots were stored at $-20°$ C. in plastic tubes.

Serum Dilution for PCA

The antiserum for sensitization was diluted so that an ID injection of 0.1 ml into control animals would give an average score of a single spot of between 2.0-3.5 using a 4 point scoring system.

Method (A) SENSITIZATION: The rats were anaesthetized with Nembutal (40-60 mg/kg i.p.) and were then sensitized by four ID injections (0.1 ml each) on their shaved backs. The animals were then left for a period of three days to develop sensitization.

(B) CHALLENGE: The sensitized rats were dosed orally or intraveneously with the drug immediately prior to intraveneous challenge via the superficial penile vein with 1 ml of an antigen/Evans blue mixture (1 mg albumen egg powder in 0.5 ml saline plus 0.5 ml of 1% Evans blue). The injections were speeded up by using an automatic 1 ml self-filling glass syringe. The "challenged" rats were killed after 30 minutes, (usually pithed) and their skin on the dorsal surface was removed. The degree and area of blueing, proportional to the anaphylactic reaction was assessed on a four point scoring system.

Calculations

1. Total scores for sites 1,2,3 and 4=X
2. Mean value of X for each group=$\overline{X}$
3. $\overline{X}$ t=$\overline{X}$ for test group
   $\overline{X}$ c=$\overline{X}$ for control group 4. % inhibition = $\dfrac{\overline{X}c - \overline{X}t}{\overline{X}c} \times \dfrac{100}{1}$ 5. $ED_{50}$=dose of drug giving 50% inhibition.

$ED_{50}$ values for the compounds tested in the passive cutaneous anaphylaxis screen (in rats) are as follows:

| Compound of | ED 50 | |
|---|---|---|
| Example | mg/kg I.V. | mg/kg p.O. |
| 2 | 0.29 | 0.63 |
| 4 | 0.57 | 3.74 |
| 5 | — | 0.096 |
| 6 | 0.0075 | 0.47 |
| 8 | 0.12 | 1.13 |
| 9 | — | 1.72 |
| 10 | 0.069 | 0.11 |
| 12 | 1.22 | — |
| 14 | 0.091 | ≈10 |
| 16 | 0.016 | 0.27 |
| 18 | 0.027 | 0.34 |
| 20 | 0.038 | 0.14 |
| 22 | 0.023 | 0.033 |
| 24 | 0.29 | — |
| 26 | 0.046 | 0.14 |

| Compound of Example | ED 50 mg/kg I.V. | mg/kg p.O. |
|---|---|---|
| 28 | 0.03 | — |
| 32 | 0.025 | 0.08 |
| 35 | 0.42 | — |

The data in the Table clearly shows that the compounds of the invention possess antiallergic activity.

Various modifications of the products and methods of the invention may be made without departing from the spirit or scope thereof and it is to be understood that the invention is intended to be limited only as defined in the appended claims.

We claim:

1. A compound selected from the group consisting of a compound of the formula

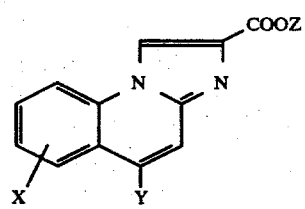

wherein Y is hydrogen, X is selected from the group consisting of hydrogen, halogen and alkoxy of 1 to 5 carbon atoms, Z is selected from the group consisting of hydrogen, alkyl of 1 to 5 carbon atoms, alkyl, of 1 to 5 carbon atoms substituted with two hydroxyls or protected hydroxyls and

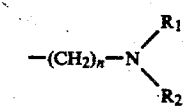

n is an integer from 1 to 6 and $R_1$ and $R_2$ are individually alkyl of 1 to 5 carbon atoms and taken together with the nitrogen to which they are attached form a heterocyclic ring selected from the group consisting of pyrrolidino, piperidino, morpholino, piperazinyl, N-methyl-piperazinyl, N-ethyl-piperazinyl, N-propyl-piperazinyl and N-butyl-piperazinyl and non-toxic, pharmaceutically acceptable salts thereof.

2. A compound of claim 1 wherein X is selected from the group consisting of hydrogen, chlorine and methoxy and Z is selected from the group consisting of hydrogen and alkyl of 1 to 5 carbon atoms.

3. A compound of claim 2 wherein Z is hydrogen or alkyl of 1 to 3 carbon atoms.

4. A compound of claim 3 wherein Z is selected from the group consisting of hydrogen and ethyl.

5. A compound of claim 1 selected from the group consisting of imidazo-[1,2-a]-quinoline-2-carboxylic acid and salts thereof.

6. A compound of claim 1 selected from the group consisting of 8-chloroimidazo-[1,2-a]-quinoline-2-carboxylic acid and salts thereof.

7. A compound of claim 1 selected from the group consisting of 8-methoxyimidazo-[1,2-a]-quinoline-2-carboxylic acid and salts thereof.

8. An antiallergic and bronchodilatory composition comprising an antiallergically and bronchodilatory effective amount of at least one compound of claim 1 and an inert pharmaceutical carrier.

9. A composition of claim 8 wherein X is selected from the group consisting of hydrogen, chlorine and methoxy and Z is selected from the group consisting of hydrogen and alkyl of 1 to 5 carbon atoms.

10. A composition of claim 8 wherein Z is hydrogen or alkyl of 1 to 3 carbon atoms.

11. A composition of claim 8 wherein Z is selected from the group consisting of hydrogen and ethyl.

12. A method of relieving allergic symptoms in warm-blooded animals comprising administering to warm-blooded animals on antiallergically effective amount of a compound of claim 1.

13. A method of claim 12 wherein X is selected from the group consisting of hydrogen, chlorine and methoxy and Z is selected from the group consisting of hydrogen and alkyl of 1 to 5 carbon atoms.

14. A method of claim 12 wherein Z is hydrogen or alkyl of 1 to 3 carbon atoms.

15. A method of claim 12 wherein Z is selected from the group consisting of hydrogen and ethyl.

16. A method of claim 12 selected from the group consisting of imidazo-[1,2-a]-quinoline-2-carboxylic acid and salts thereof.

17. A method of claim 12 selected from the group consisting of 8-chloroimidazo-[1,2-a]-quinoline-2-carboxylic acid and salts thereof.

18. A method of claim 12 selected from the group consisting of 8-methoxyimidazo-[1,2-a]-quinoline-2-carboxylic acid and salts thereof.

19. A compound of claim 1 selected from the group consisting of 7-chloro-imidazo-[1,2-a]-quinoline-2-carboxylic acid and salts thereof.

20. A compound of claim 1 selected from the group consisting of 7-methoxy-imidazo-[1,2-a]-quinoline-2-carboxylic acid and salts thereof.

21. A compound of claim 1 selected from the group consisting of 6-chloro-imidazo-[1,2-a]-quinoline-2-carboxylic acid and salts thereof.

22. A method of claim 12 selected from the group consisting of 7-chloro-imidazo-[1,2-a]-quinoline-2-carboxylic acid and salts thereof.

23. A method of claim 12 selected from the group consisting of 7-methoxy-imidazo-[1,2-a]-quinoline-2-carboxylic acid and salts thereof.

24. A method of claim 12 selected from the group consisting of 6-chloro-imidazo-[1,2-a]-quinoline-2-carboxylic acid and salts thereof.

* * * * *